United States Patent
Ventura et al.

(10) Patent No.: US 10,209,193 B2
(45) Date of Patent: Feb. 19, 2019

(54) NANOMATERIAL-BASED SUBSTRATES FOR CHEMICAL SENSORS USING SURFACE ENHANCED RAMAN SPECTROSCOPY

(71) Applicants: Darryl N. Ventura, Houston, TX (US); Sankaran Murugesan, Katy, TX (US); Valery N. Khabashesku, Houston, TX (US); Radhika Suresh, Sugar Land, TX (US)

(72) Inventors: Darryl N. Ventura, Houston, TX (US); Sankaran Murugesan, Katy, TX (US); Valery N. Khabashesku, Houston, TX (US); Radhika Suresh, Sugar Land, TX (US)

(73) Assignee: BAKER HUGHES, A GE COMPANY, LLC, Houston, TX (US)

(*) Notice: Subject to any disclaimer, the term of this patent is extended or adjusted under 35 U.S.C. 154(b) by 0 days.

(21) Appl. No.: 15/143,886

(22) Filed: May 2, 2016

(65) Prior Publication Data
US 2017/0315061 A1  Nov. 2, 2017

(51) Int. Cl.
*G01N 21/65* (2006.01)

(52) U.S. Cl.
CPC ................... *G01N 21/658* (2013.01)

(58) Field of Classification Search
CPC .......................... G01N 21/658; G01N 21/554
See application file for complete search history.

(56) References Cited

U.S. PATENT DOCUMENTS

| 6,226,082 B1* | 5/2001 | Roe ..................... G01N 21/658 250/339.12 |
| 8,470,946 B1* | 6/2013 | Carlson ................ C08F 132/06 525/326.1 |
| 2007/0153267 A1* | 7/2007 | Wang ................... G01N 21/658 356/301 |
| 2008/0006121 A1* | 1/2008 | Keller ..................... B01J 23/89 75/255 |
| 2009/0263485 A1 | 10/2009 | Li et al. |
| 2010/0009338 A1 | 1/2010 | Zhang et al. |

(Continued)

FOREIGN PATENT DOCUMENTS

WO   2015173432 A1   11/2015

OTHER PUBLICATIONS

Darryl Ventura, "Assembly of cross-linked multi-walled carbon nanotube mats", Nov. 12, 2009, Direct Sicence.*

(Continued)

*Primary Examiner* — Maurice Smith
(74) *Attorney, Agent, or Firm* — Cantor Colburn LLP

(57) ABSTRACT

A method and apparatus for estimating a concentration of chemicals in a fluid flowing in a fluid passage is disclosed. A sample of the fluid is placed on a substrate comprising a first layer of carbon nanotubes and a second layer of metal nanowires. An energy source radiates the fluid sample with electromagnetic radiation at a selected energy level, and a detector measures an energy level of radiation emitted from the fluid sample in response to the electromagnetic radiation. A processor determines a Raman spectrum of the fluid sample from the energy level of the emitted radiation and estimates the concentration of a selected chemical in the fluid sample based on the Raman spectrum.

18 Claims, 5 Drawing Sheets

(56) References Cited

U.S. PATENT DOCUMENTS

| | | |
|---|---|---|
| 2010/0085565 A1 | 4/2010 | Koo et al. |
| 2010/0190661 A1 | 7/2010 | Lee et al. |
| 2011/0043800 A1* | 2/2011 | Sardashti ............. G01N 21/658 356/301 |
| 2011/0063613 A1 | 3/2011 | Sun et al. |
| 2013/0172207 A1* | 7/2013 | Dai ...................... G01N 33/553 506/9 |
| 2014/0373649 A1 | 12/2014 | Harrell et al. |
| 2015/0077743 A1 | 3/2015 | Maznichenko et al. |
| 2015/0207106 A1* | 7/2015 | Pei ...................... H01L 51/0048 257/40 |
| 2016/0116414 A1* | 4/2016 | Day ................... B01D 53/1425 356/36 |
| 2017/0074799 A1 | 3/2017 | Peterman et al. |
| 2017/0315061 A1 | 11/2017 | Ventura et al. |

OTHER PUBLICATIONS

Katsuhiko Ariga, "Layer-by-layer assembly as a versatile bottom-up nanofabrication technique for exploratory research and realistic application",Physical Chemistry Chemical Physics, Mar. 1, 2007.*

Altun et al.; "Femtomolar molecular detection with CNT based SERS substrate," Proc. of SPIE vol. 9168, 2014, 916809-1-916809-9.

Murray et al.; "Amine Vapor Sensing with Silver Mesowires," Nano Letters, 2004, vol. 4, No. 4, pp. 665-670.

PCT International Search Report and Written Opinion; International Application No. PCT/US2017/030556; International Filing Date: May 2, 2017; dated Jul. 26, 2017; pp. 1-13.

* cited by examiner

US 10,209,193 B2

NANOMATERIAL-BASED SUBSTRATES FOR CHEMICAL SENSORS USING SURFACE ENHANCED RAMAN SPECTROSCOPY

BACKGROUND

The present disclosure is directed to a method and apparatus for detecting a concentration of chemicals in a process stream in a refinery and, in particular, to using Surface Enhanced Raman Spectroscopy (SERS) to detect concentrations of corrosive chemicals in hydrocarbon fluids.

Hydrocarbon fluids that are produced from a reservoir include a rich mixture of chemicals, some of which are provided naturally from the formation and some of which end up in the fluid during various stages of petroleum exploration, completion and/or production. Refineries receive feedstocks that include the hydrocarbon fluids and extract or separate out unwanted chemicals. Refinery feedstocks and process streams used in refineries often contain contaminant amines (e.g., from shale oils or upstream $H_2S$ scavenger treatments) which contribute to amine-HCl salt formation in crude unit towers and overhead towers of the refineries. Amine-HCl salt corrosion is the most common form of corrosion impacting refinery processing units, and monoethanolamine (MEA) is the most common and problematic of the contaminant amines. In order to extract or separate a chemical such as MEA from process streams, it is necessary to detect and determine the concentrations of the chemical in the process stream. Current methods of chemical concentration detection can take from days to weeks to obtain results. A rapid monitoring field method for easily measuring amine levels in process streams is therefore needed to allow an operator to take prompt and appropriate action to mitigate corrosion risk in refinery parts.

BRIEF DESCRIPTION

In one aspect, the present invention provides a method of estimating a concentration of chemicals in a fluid flowing in a fluid passage, including: placing a sample of the fluid flowing in the fluid passage on a substrate comprising a first layer of carbon nanotubes and a second layer of metal nanowires; radiating the fluid sample with electromagnetic radiation at a selected energy level; measuring a Raman spectrum emitted from the fluid sample in response to the electromagnetic radiation; and estimating the concentration of a selected chemical in the sample fluid from the Raman spectrum.

In another aspect, the present invention provides an apparatus for estimating a concentration of a chemical in a fluid passage, including: a substrate for supporting a fluid sample from the fluid passage, the substrate comprising a first layer of carbon nanotubes and a second layer of metal nanowires; an energy source for directing a beam of electromagnetic energy at a selected energy level at the fluid sample; a detector for measuring an energy level of radiation emitted from the fluid sample in response to the beam of electromagnetic energy; and a processor configured to: determine a Raman spectrum of the fluid sample from the energy level of the emitted radiation, and estimate the concentration of a selected chemical in the fluid sample based on the Raman spectrum.

In yet another aspect, the present invention provides a method for characterizing a corrosive chemical in a fluid flowing in a fluid passage, including: placing a sample of the fluid on a substrate comprising a first layer of carbon nanotubes and a second layer of metal nanowires; radiating the fluid sample with electromagnetic radiation at a selected energy level; measuring a Raman spectrum emitted from the fluid sample in response to the electromagnetic radiation; and characterizing a concentration of the corrosive chemical in the fluid sample from the Raman spectrum.

BRIEF DESCRIPTION OF THE DRAWINGS

The following descriptions should not be considered limiting in any way. With reference to the accompanying drawings, like elements are numbered alike.

DETAILED DESCRIPTION

A detailed description of one or more embodiments of the disclosed apparatus and method are presented herein by way of exemplification and not limitation with reference to the Figures.

Figure 1:
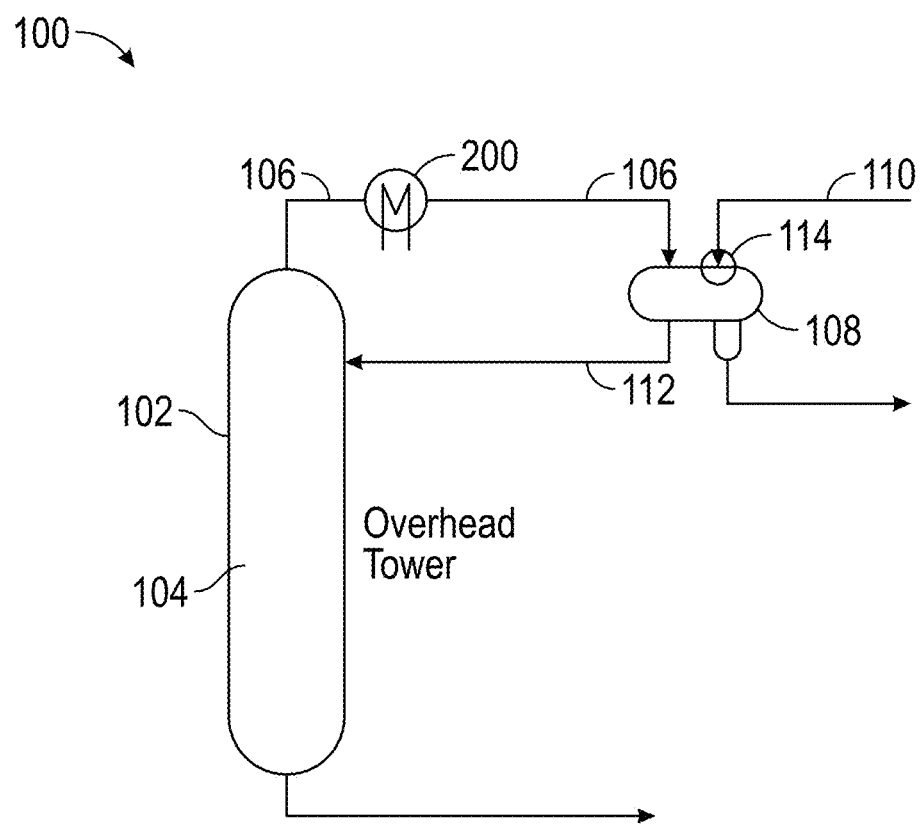
FIG. 1 shows a section of a conduit or fluid passage for flow of fluid according to one embodiment of the present invention.

FIG. 1 shows a section 100 of a refinery through which fluid 104 is generally stored and can be tested according to one embodiment of the present invention. The refinery section 100 includes an overhead tower 102 that stores the fluid 104. The fluid is generally a hydrocarbon fluid 104 that has been extracted from a reservoir in an earth formation. The fluid 104 may further include an amine such as monoethanolamine (MEA) which is added to the fluid prior to storing the fluid 104 in the overhead tower 102. While MEA is added in order to extract hydrogen sulfide ($H_2S$) from the hydrocarbon fluid 104, the MEA can react with hydrochloric acid (HCl) that may be present in the hydrocarbon fluid 104 to produce salts that can be corrosive to components of the refinery, such as the overhead tower 102, etc. Other amines that have a corrosive effect and which can be used in the fluid 104 may include, but are not limited to, dimethylethanolamine (DMEA), methylamine (MA) and methyl diethanolamine (MDEA). In order to prevent a selected amine from corroding the overhead tower 102, a corrosion inhibitor 110 targeted to the selected amine can be introduced into the fluid passage at a mixing chamber 108. It is desired to introduce an amount of corrosion inhibitor 110 that is proportional to the amount of amine.

Fluid analyzer 200 is used to determine a concentration of the amine in the fluid 104. A fluid passage 106 such as a pipe or conduit transports the fluid 104 from the overhead tower 102 to the fluid analyzer 200. In one aspect, the fluid passage 106 includes the fluid analyzer 200 as an integrated component of the fluid passage 102. Alternatively, the fluid analyzer 200 can be a component connected to a side of the fluid passage 106 and a sample of fluid 104 can be diverted from the fluid passage 102 into the fluid analyzer 200. Upon exiting the fluid analyzer 200, the fluid 104 can be delivered by the fluid passage 106 to a mixing chamber 108. A valve 114 can be opened or closed to a selected degree to provide a suitable corrosion inhibitor 110 into the mixing chamber 108 in proportion with the amount of the amine in the fluid as determined by the fluid analyzer 200. The mixed fluid can be restored to the overhead tower 102 via return fluid passage 112.

Figure 2:
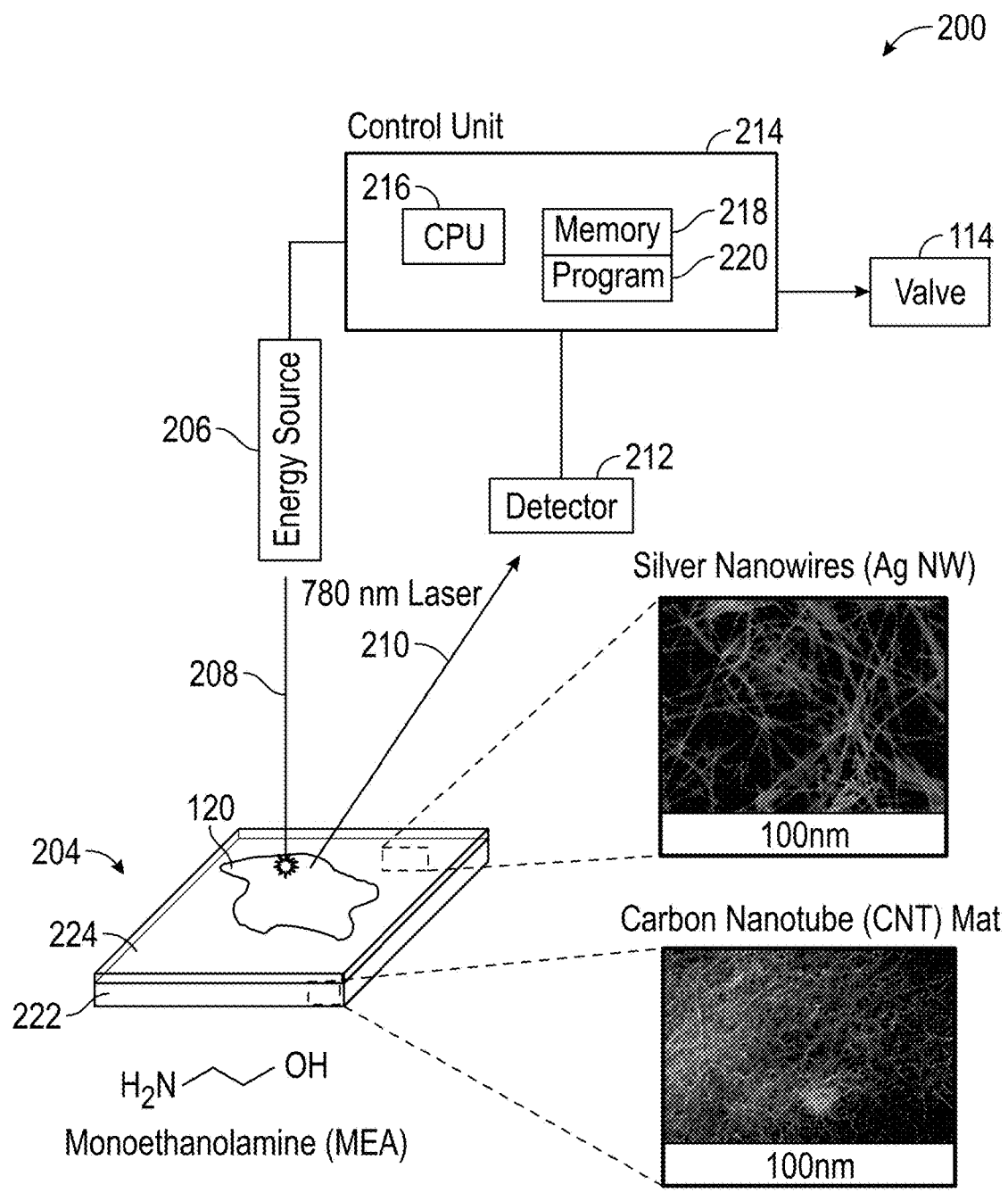
FIG. 2 shows a detailed view of the fluid analyzer of FIG. 1 according to one embodiment of the present invention.

FIG. 2 shows a detailed view of the fluid analyzer 200 of FIG. 1 according to one embodiment of the present invention. The fluid analyzer 200 includes an apparatus for performing Surface Enhanced Raman Spectroscopy (SERS) on a fluid sample 120 drawn from fluid 104 in order to detect trace amounts of a selected chemical in the fluid sample 120. SERS is a surface-sensitive detection technique that is used to detect a composition of analyte adsorbed on rough metal surfaces or nanostructures surfaces. The methods disclosed herein provide enhancements in Raman signals of adsorbed molecules to the order of $10^4$ to $10^6$ which help in detecting analytes at parts per million (ppm) levels. In the fluid analyzer 200 of the present invention, the fluid sample 120 is deposited on a substrate 204 in a liquid phase and electromagnetic energy 208 is directed at the fluid sample 120 from an energy source 206. In one embodiment, the energy source 206 is a laser and the electromagnetic energy 208 is a monochromatic beam provided at a frequency or energy level that is attuned to at least one of a vibrational or rotational excitation of the selected chemical within the fluid sample 120. The electromagnetic energy 208 excites the electrons of the chemical within the fluid sample 120 to a virtual energy state. As the selected chemical drops back into a lower energy state, it emits photons 210 that can be either lower energy (Stokes scattering) or higher energy (anti-Stokes scattering) than the energy of the incident electromagnetic energy 208. The emitted photons 210 are received at detector 212. The detector 212 generates signals indicative of the energy of the received photon 210 which are sent to control unit 214 for processing.

The control unit 214 includes a processor 216, a memory storage device 218, generally a solid-state memory storage device, and one or more programs 220 stored in the memory storage device 218 and accessible to the processor 216. When the one or more programs 220 are executed or run by the processor 216, the processor 216 produces a spectrum of the emitted photons. The spectrum can be observed or reviewed in order to identify chemicals and relative chemical concentrations within the fluid sample 120. The processor 216 can estimate a concentration level of chemicals with the fluid sample 120 and provide control signals to various components to control a level of the chemicals. In one embodiment, the processor 216 can provide a control signal to valve 114 in order to add a corrosion inhibitor 110 in an amount that corresponds to or is proportional to the concentration of the chemical identified by the fluid analyzer 200. Thus, corrosion inhibitor 110 can be added in order to neutralize the MEA in the hydrocarbon fluid 104 of FIG. 1. Although only one valve 114 for adding corrosion inhibitor 112 is shown in FIG. 1, multiple valves for adding corrosion inhibitor 112 can be provided at various locations of the fluid passage in alternate embodiments. Thus the control unit 214 can take an action to control or prevent corrosion at various locations of the refinery. While the control unit 214 is described as controlling valve 114, in alternate embodiments, an operator can review the detected concentration of the chemical and determine an amount of corrosion inhibitor 112 to add to the fluid and/or control the valve 114.

Returning to the substrate 204 of the fluid analyzer 200, the substrate 204 is a composite of conducting carbon materials (such as single-walled carbon nanotubes, double-walled carbon nanotubes, and multi-walled carbon nanotubes), noble metal nanowires, metal oxides and/or other plasmonic metals. The substrate includes a first layer 222 that can include the conductive carbon and a second layer 224 that can include the noble metal nanowires, metal oxides and/or other plasmonic metals. In a particular embodiment, the first layer 222 includes carbon nanotubes (CNTs) and the second layer 224 includes a silver nanowire (Ag NW). The first layer 222 can be formed by filtering CNTs from a suspension. The carbon nanotubes of the first layer 22 can be chemically cross-linked CNTs implemented in the form of flexible carbon nanotube mats, thereby providing a flexible yet durable substrate 204. In various embodiments, the second layer 224 can include metal nanowires, silver nanowires, metal nanowires with metal nanoparticles, and silver nanowires with metal nanoparticles. The metal nanoparticles may be silver nanoparticles and generally have a different aspect ratio than the nanowires of the second layer 224. In an illustrative embodiment, the metal nanowires are silver nanowires. The silver nanowires of the second layer 224 are deposited or formed on top of the first layer 222 in order to coat the first layer 222. The substrate 204 takes advantage of a synergistic SERS effect between the CNTs of the first layer 222 and the silver nanowires of the second layer 224 to enhance the SERS signal. The substrate 204 is stable over a wide range of pH levels and corrosive chemical environments. Due to its flexibility, the substrate 204 can be deformed to fit into a desired shape that suits or conforms to a selected form factor of the fluid analyzer 200. For example, the substrate 204 can be rolled into a scroll, enabling the fluid analyzer to be miniaturized so that it can be implemented as a compact sensor usable to detect chemicals in real-time. The fluid sample 120 is placed on top of the second layer 224 during the testing process. The composition of the CNT-Ag NW substrate 204 enhances the Raman signal of MEA, as discussed below with respect to FIG. 3.

Figure 3:
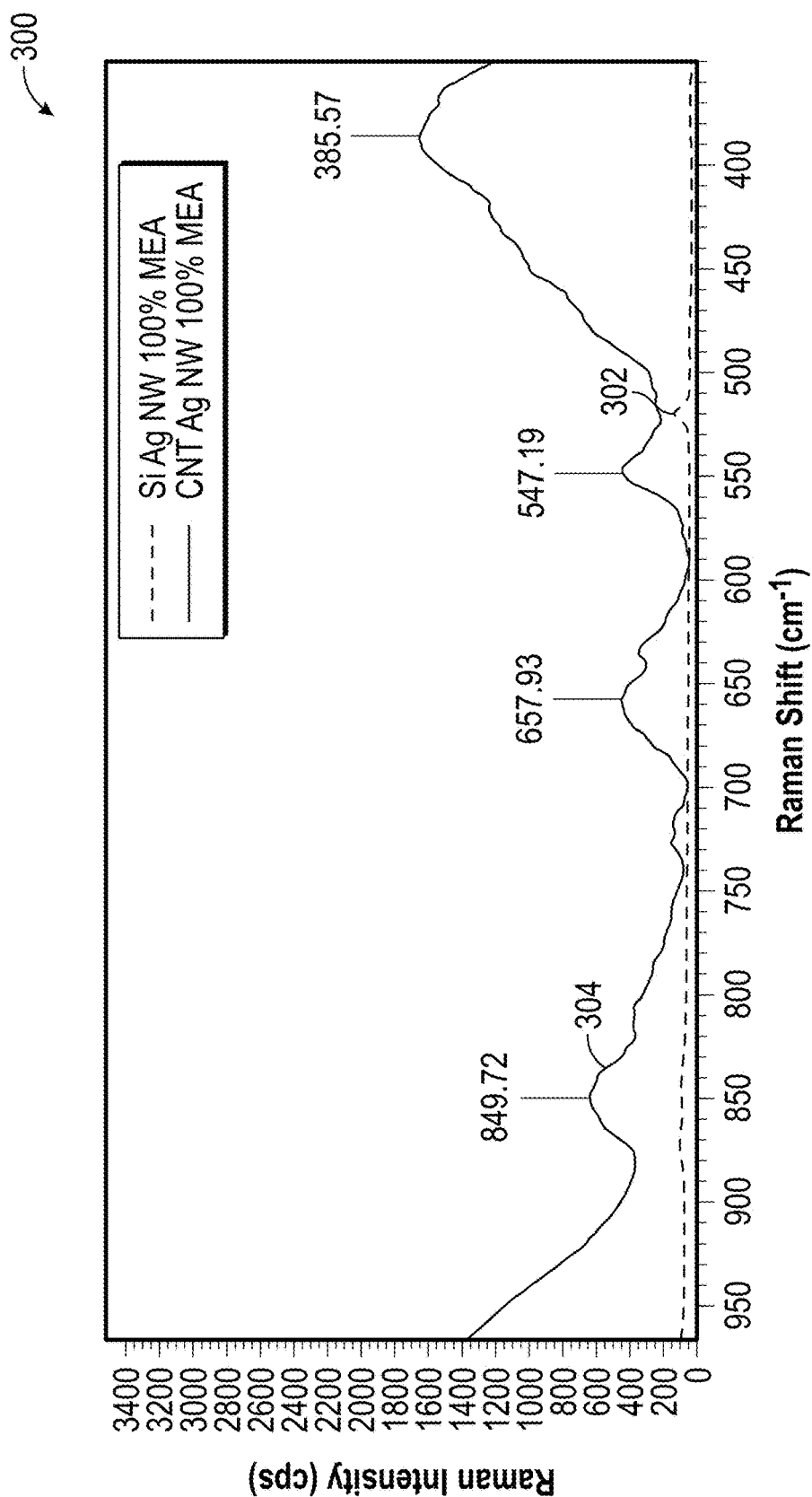
FIG. 3 shows various Raman spectroscopy spectra for a selected chemical obtained by performing SERS on the chemical using different substrates.

FIG. 3 shows various Raman spectroscopy spectra 300 for a selected chemical obtained by performing SERS on the chemical using different substrates. Spectrum 302 represents a spectrum of 100% MEA obtained using SERS with a Silicon Ag NW substrate. Spectrum 304 represents a spectrum of 100% MEA obtained using SERS with a CNT Ag NW substrate. Raman intensity is shown along the ordinate axis and Raman shift is shown along the abscissa. FIG. 3 clearly shows that the peaks of spectrum 304 are more enhanced than the peaks of spectrum 302 and provides a larger signal-to-noise ratio. Using typical Si substrates, the identifying peaks of spectrum 320 have a lower intensity and are often difficult to discern from signal noise. The signal obtained with the CNT Ag NW substrate is approximately 10 times greater than the signal obtained with conventional substrates. Therefore, the CNT Ag NW substrate can be useful in order to identify low concentrations of MEA within the fluid sample 120. In one embodiment, trace amounts of MEA can be detected at concentrations as low as 123 ppm. Such low detection limits enable the sensor technology of the present invention to provide accurate results at field locations, such as in refineries, etc.

Figure 4:
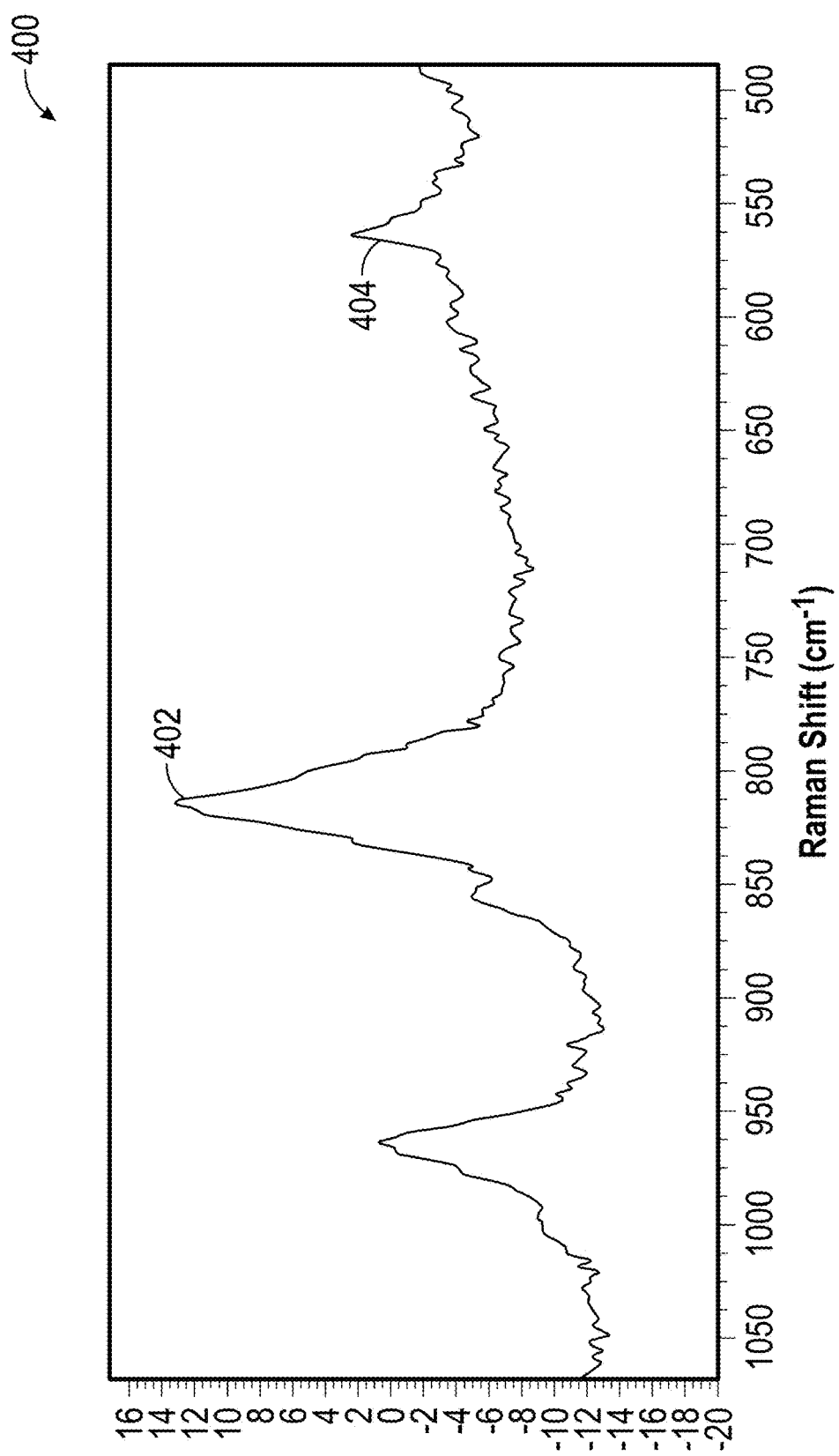
FIG. 4 shows a Raman spectrum for 123 ppm MEA on CNT/Ag NW SERS substrate of FIG. 2.

FIG. 4 shows a Raman spectrum 400 for 123 ppm MEA on CNT/Ag NW SERS substrate of FIG. 2. Raman intensity is shown along the ordinate axis and Raman shift is shown along the abscissa. Peak 402 in the 825 $cm^{-1}$ region and peak 404 in the 550 $cm^{-1}$ region are indicative of the presence of MEA. The spectrum 400 demonstrates that the presence of MEA at about 123 ppm can be reliably detected using the CNT-Ag NW substrate in a SERS testing process.

Figure 5:
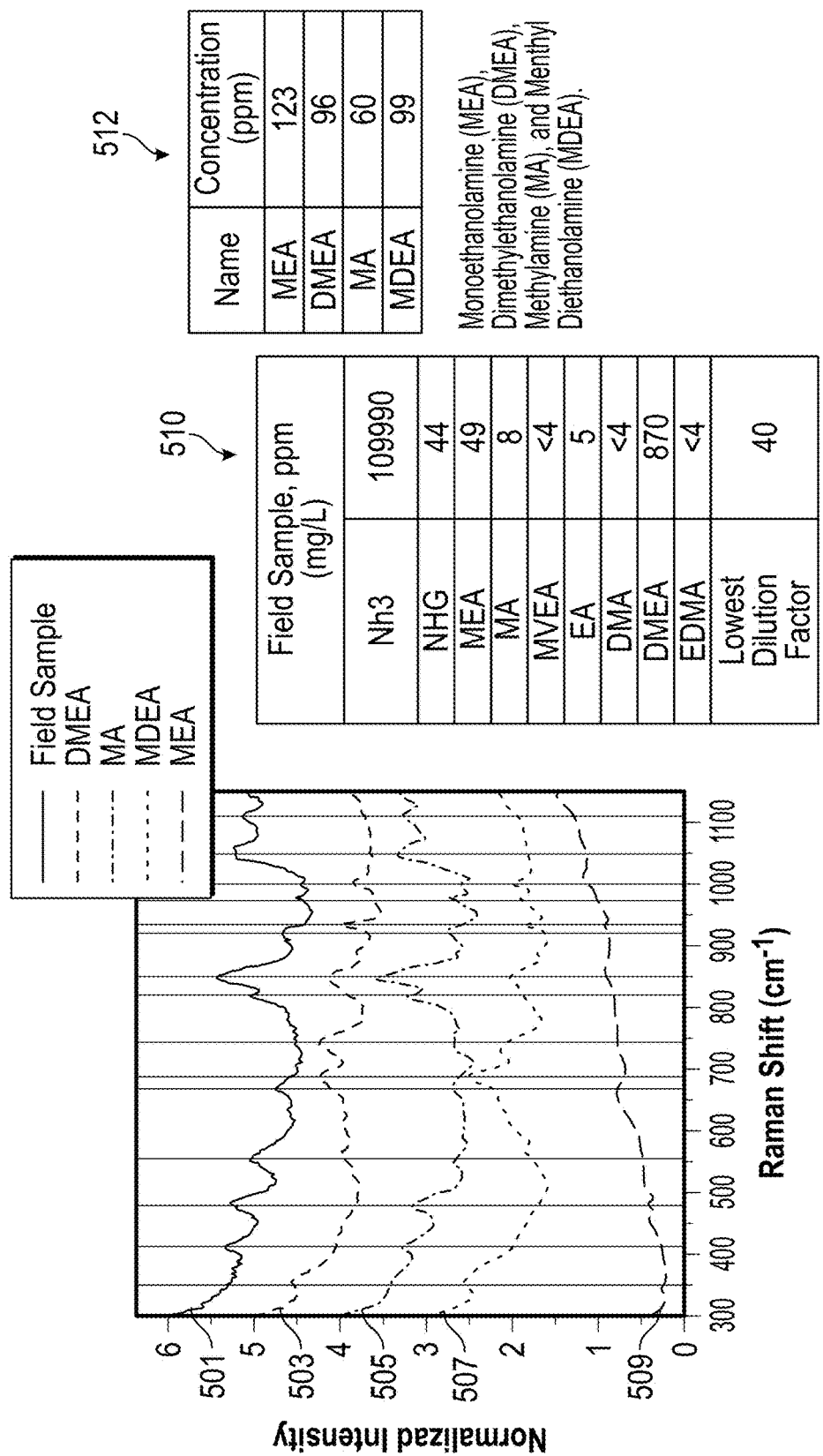
FIG. 5 shows Raman spectra for various diluted amine samples.

The use of the substrate disclosed herein enables selective and quantitative detection amines in addition to MEA. FIG. 5, for example, shows Raman spectra for various diluted amine samples. A spectrum 501 for fluid sample is shown.

Spectra 503, 505, 507, 509 indicate the presence of dimethylethanolamine (DMEA), methylamine (MA), methyl diethanolamine (MDEA) and monoethanolamine (MEA), respectively. Concentrations determine using the SERS testing with the substrate disclosed herein are shown in table 510 in milligrams per liter (mg/L) and in table 512 in parts per million (ppm).

While the present invention has been described with respect to refining equipment, the SERS testing process can be performed at refineries, a borehole location, or other suitable location. The sensors disclosed herein can be used to detect the presence of completion fluid in a formation fluid before a well is transitioned into the full production stage. Also, such the methods disclosed herein can be used to detect trace amounts of corrosive chemical that are detrimental to downhole equipment.

Set forth below are some embodiments of the foregoing disclosure:

Embodiment 1

A method of estimating a concentration of chemicals in a fluid flowing in a fluid passage, including: placing a sample of the fluid flowing in the fluid passage on a substrate comprising a first layer of carbon nanotubes and a second layer of metal nanowires; radiating the fluid sample with electromagnetic radiation at a selected energy level; measuring a Raman spectrum emitted from the fluid sample in response to the electromagnetic radiation; estimating the concentration of a selected chemical in the sample fluid from the Raman spectrum; and selecting a corrosion inhibitor to the fluid flowing in the fluid passage based on the concentration of the selected chemical.

Embodiment 2

The method of embodiment 1, wherein the carbon nanotubes of the first layer form a carbon nanotube mat.

Embodiment 3

The method of embodiment 1, wherein the silver nanowires of the second layer are grown on the carbon nanotubes of the first layer.

Embodiment 4

The method of embodiment 1, wherein the substrate is a flexible substrate.

Embodiment 5

The method of embodiment 1, wherein the selected chemical is at least one of (i) an amine; (ii) a sulfur compound; (iii) an amino alcohols; and (iv) an amino thiol.

Embodiment 6

The method of embodiment 1, wherein the selected chemical is monoethanolamine (MEA).

Embodiment 7

The method of embodiment 1, wherein the second layer comprises at least one of: (i) silver nanowires; (ii) metal nanowires and metal nanoparticles; and (iii) silver nanowires and metal nanoparticles.

Embodiment 8

The method of embodiment 1, wherein the fluid passage is at least one of: (i) a fluid passage at a downstream location of a completion process; (ii) a fluid passage at a downstream location of a crude wash process; and (iii) a fluid passage of an overhead tower of a petroleum refinery.

Embodiment 9

An apparatus for estimating a concentration of a chemical in a fluid passage, including: a substrate for supporting a fluid sample from the fluid passage, the substrate comprising a first layer of carbon nanotubes and a second layer of metal nanowires; an energy source for directing a beam of electromagnetic energy at a selected energy level at the fluid sample; a detector for measuring an energy level of radiation emitted from the fluid sample in response to the beam of electromagnetic energy; and a processor configured to: determine a Raman spectrum of the fluid sample from the energy level of the emitted radiation, estimate the concentration of a selected chemical in the fluid sample based on the Raman spectrum, and select a concentration of a corrosion inhibitor in the fluid based on the determined concentration of the selected chemical.

Embodiment 10

A method for characterizing a corrosive chemical in a fluid flowing in a fluid passage, including: placing a sample of the fluid on a substrate comprising a first layer of carbon nanotubes and a second layer of metal nanowires; radiating the fluid sample with electromagnetic radiation at a selected energy level; measuring a Raman spectrum emitted from the fluid sample in response to the electromagnetic radiation; and characterizing a concentration of the corrosive chemical in the fluid sample from the Raman spectrum.

The use of the terms "a" and "an" and "the" and similar referents in the context of describing the invention (especially in the context of the following claims) are to be construed to cover both the singular and the plural, unless otherwise indicated herein or clearly contradicted by context. Further, it should further be noted that the terms "first," "second," and the like herein do not denote any order, quantity, or importance, but rather are used to distinguish one element from another. The modifier "about" used in connection with a quantity is inclusive of the stated value and has the meaning dictated by the context (e.g., it includes the degree of error associated with measurement of the particular quantity).

The teachings of the present disclosure may be used in a variety of well operations. These operations may involve using one or more treatment agents to treat a formation, the fluids resident in a formation, a wellbore, and/or equipment in the wellbore, such as production tubing. The treatment agents may be in the form of liquids, gases, solids, semi-solids, and mixtures thereof. Illustrative treatment agents include, but are not limited to, fracturing fluids, acids, steam, water, brine, anti-corrosion agents, cement, permeability modifiers, drilling muds, emulsifiers, demulsifiers, tracers, flow improvers etc. Illustrative well operations include, but are not limited to, hydraulic fracturing, stimulation, tracer injection, cleaning, acidizing, steam injection, water flooding, cementing, etc.

While the invention has been described with reference to an exemplary embodiment or embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the claims. Also, in the drawings and the description, there have been disclosed exemplary embodiments of the invention and, although specific terms may have been employed, they are unless otherwise stated used in a generic and descriptive sense only and not for purposes of limitation, the scope of the invention therefore not being so limited.

What is claimed is:

1. A method of estimating a concentration of chemicals in a fluid flowing in a fluid passage, comprising:
    forming a substrate comprising a first layer made from unaligned carbon nanotubes filtered from a suspension and chemically cross-linked to form the first layer and a second layer of metal nanowires directly deposited on top of the first layer to coat the first layer;
    placing a sample of the fluid flowing in the fluid passage on the substrate;
    radiating the fluid sample with electromagnetic radiation at a selected energy level;
    measuring a Raman spectrum emitted from the fluid sample in response to the electromagnetic radiation; and
    estimating the concentration of a selected chemical in the sample fluid from the Raman spectrum.

2. The method of claim 1, wherein the carbon nanotubes of the first layer form a carbon nanotube mat.

3. The method of claim 1, wherein the metal nanowires of the second layer coat the carbon nanotubes of the first layer.

4. The method of claim 1, wherein the substrate is a flexible substrate.

5. The method of claim 1, wherein the selected chemical is at least one of (i) an amine; (ii) a sulfur compound; (iii) an amino alcohols; and (iv) an amino thiol.

6. The method of claim 1, wherein the selected chemical is monoethanolamine (MEA).

7. The method of claim 1, wherein the second layer comprises at least one of: (i) silver nanowires; (ii) metal nanowires and metal nanoparticles; and (iii) silver nanowires and metal nanoparticles.

8. The method of claim 1, wherein the fluid passage is at least one of: (i) a fluid passage at a downstream location of a completion process; (ii) a fluid passage at a downstream location of a crude wash process; and (iii) a fluid passage of an overhead tower of a petroleum refinery.

9. An apparatus for estimating a concentration of a chemical in a fluid passage, comprising:
    a substrate comprising a first layer of unaligned carbon nanotubes and a second layer of metal nanowires directly deposited on top of the first layer to coat the first layer, the carbon nanotubes of the first layer being filtered from a suspension and chemically cross-linked;
    an energy source for directing a beam of electromagnetic energy at a selected energy level at a fluid sample from the fluid passage on a surface of the substrate;
    a detector for measuring an energy level of radiation emitted from the fluid sample in response to the beam of electromagnetic energy; and
    a processor configured to:
        determine a Raman spectrum of the fluid sample from the energy level of the emitted radiation, and
        estimate the concentration of a selected chemical in the fluid sample based on the Raman spectrum.

10. The apparatus of claim 9, wherein the carbon nanotubes of the first layer form a carbon nanotube mat.

11. The apparatus of claim 9, wherein the metal nanowires of the second layer are deposited onto the first layer.

12. The apparatus of claim 9, wherein the substrate is a flexible substrate.

13. The apparatus of claim 9, wherein the selected chemical is at least one of (i) an amine; (ii) a sulfur compound; (iii) an amino alcohols; (iv) an amino thiol; and (v) monoethanolamine (MEA).

14. The apparatus of claim 9, wherein the metal nanowires further comprise at least one of: (i) silver nanowires; (ii) metal nanowires and metal nanoparticles; and (iii) silver nanowires and metal nanoparticles.

15. The apparatus of claim 9, wherein the fluid passage is one of: (i) a fluid passage at a downstream location of a completion process; (ii) a fluid passage at a downstream location of a crude wash process; and (iii) a fluid passage of an overhead tower of a petroleum refinery.

16. A method for characterizing a corrosive chemical in a fluid flowing in a fluid passage, comprising:
    forming a substrate comprising a first layer made from unaligned carbon nanotubes filtered from a suspension and chemically cross-linked to form the first layer and a second layer of metal nanowires directly deposited on top of the first layer to coat the first layer;
    placing a sample of the fluid on the substrate;
    radiating the fluid sample with electromagnetic radiation at a selected energy level;
    measuring a Raman spectrum emitted from the fluid sample in response to the electromagnetic radiation; and
    characterizing a concentration of the corrosive chemical in the fluid sample from the Raman spectrum.

17. The method of claim 16, wherein the corrosive chemical is at least one selected from the group consisting of: (i) dimethylethanolamine; (ii) methylamine; (iii) methyl diethanolamine; and (iv) monoethanolamine.

18. The method of claim 16, further comprising adding a corrosion inhibitor to the fluid flowing in the fluid passage based on the concentration of the corrosive chemical.

* * * * *